United States Patent [19]

Newman

[11] Patent Number: 5,147,854
[45] Date of Patent: Sep. 15, 1992

[54] TGF-B COMPOSITIONS AND METHOD

[75] Inventor: Michael J. Newman, Upper Montclair, N.J.

[73] Assignee: Hoffmann-La Roche Inc., Nutley, N.J.

[21] Appl. No.: 527,215

[22] Filed: May 22, 1990

[51] Int. Cl.$^5$ .............................................. A61K 37/36
[52] U.S. Cl. ........................................ 514/12; 514/2; 514/21
[58] Field of Search ................................ 514/12, 2, 21

[56] References Cited

U.S. PATENT DOCUMENTS

| | | | |
|---|---|---|---|
| 4,326,055 | 4/1982 | Leoliger | 542/429 |
| 4,816,442 | 3/1989 | McPherson et al. | 514/12 |
| 4,863,902 | 9/1989 | Amagase et al. | 514/21 X |

OTHER PUBLICATIONS

JNCI, vol. 77, No. 5, Nov. 1986, Begin et al.
JNCI, vol. 80, No. 3, Apr. 1988, Begin et al.
Chem. Abstracts, vol. 111, 1989, 127695w, Twardzik et al.
Newman, Proc. Natl. Acad. Sci. USA, 87=5543-5547, Jul., 1990.

*Primary Examiner*—Howard E. Schain
*Attorney, Agent, or Firm*—George M. Gould; William H. Epstein; Catherine R. Roseman

[57] ABSTRACT

Transforming growth factor-beta (TGF-beta) is enhanced in its therapeutic activity by utilizing it in combination with a synergistic effective amount of a polyunsaturated fatty acid (PUFA). In a preferred embodiment, type 1 transforming growth factor beta (TGF-⊕1) exhibits enhanced anti-neoplastic activity when utilized in combination with an n=3 or n=6 polyunsaturated fatty acid. Examples of suitable unsaturated fatty acids include linoleic, alpha-linolenic, arachidonic, gamma-linolenic, dihomogammalinolenic, eicosapentaenoic and docosahexaenoic. Combinations of these agents effectively kill various human carcinoma and melanoma cell lines under defined conditions in vitro at picomolar concentrations of TGF-$\beta$1 and at $\mu$g/ml concentrations of the polyunsaturated fatty acid, levels where the respective two agents acting alone are ineffective.

16 Claims, 6 Drawing Sheets

FIG. 6 ns
TGF-β COMPOSITIONS AND METHOD

BACKGROUND

Human TGF-beta has been isolated from human blood platelets and placenta and purified to essential homogeneity using sequential gel filtration cation-exchange chromatography and high performance liquid chromatography (HPLC). The purified protein was characterized as having a molecular weight of 25,000 daltons, composed of 2 sub-units of 12,500 daltons each held together by disulfide bonds. Its molecular weight, sub-unit structure and amino acid composition differed from those of platelet derived growth factor. See European Patent Application EP 128849 (Dec. 19, 1984), priority applications U.S. Ser. No. 500,832 (Jun. 3, 1983) and U.S. Ser. No. 500,927 (Jun. 3, 1983).

An alternative method for purifying TGF-beta from platelets or conditioned media utilizes acid-ethanol extraction, cation-exchange separation on the extract, carrying out hydrophobic separations on the active fractions so as to obtain a homogeneous preparation and is described in European Patent Application 322842-A (Jul. 12, 1989). The purified product is indicated to be useful in wound healing and tissue repair.

Production of TGF-beta 1 utilizing recombinant DNA techniques is described in JP61219395 (Sep. 29, 1986) having priority from U.S. patent application Ser. No. 715,142 (Mar. 22, 1985) assigned to Genentech as well as in JP63028386 (Feb. 6, 1988) assigned to Asahi Chemical Industry Co. Ltd. Both disclosures insert the cloned human gene coding for TGF-beta 1 into eukaryotic cell lines for expression. The protein product was indicated to be useful in promoting anchorage-dependent and independent growth in cell culture.

Further suggestion as to the use of TGF-beta in wound healing is found in PCT application WO 8911293-A (Nov. 30, 1989) based on U.S. patent application Ser. No. 196,975 (May 20, 1988) where a composition containing both purified insulin-like growth factor-1 and purified TGF-beta in ratios of 1:4 to 25:1 are employed.

Polyunsaturated fatty acids have been known to exhibit cytotoxicity against tumor cells based on a proposed ability to stimulate the production of superoxide radicals. Thus Begin et al., Journal of the National Cancer Institute, 80, No. 3, 188-194 (Apr. 6, 1988) tested a series of fatty acids containing 2, 4, 5, and 6 double bonds, which were compared to gamma-linolenate (3 double bonds). The results showed that effectiveness of fatty acid induced cytotoxicity on cancer cells correlated with intracellular thiobarbituric acid-reactive material content. Gamma-linolenate and arachidonate with 3 and 4 double bonds gave the highest cytotoxicity and highest correlation. All of the experiments described in this study were carried out in the presence of serum, which contains TGF-β1. Earlier results to similar effect were reported by the same group in a publication in the Journal of the National Cancer Institute, 77, No. 5 at 1054-1062 (November, 1986). This study also demonstrated that polyunsaturated fatty acid-induced cytotoxicity was relatively specific for tumor cells. Concentrations of fatty acids which killed tumor cells had little or no effect on the growth of nontransformed cells.

SUMMARY OF THE INVENTION

The present invention relates to the synergistic enhancement of the therapeutic activity evidenced by transforming growth factor beta by co-administering a synergistic effective amount of a polyunsaturated fatty acid. A preferred form of transforming growth factor beta is known as Type 1 TGF-β or TGF-beta 1.

Type 1 transforming growth factor β (TGF-β1) is a multi-functional protein found in all mammalian tissues. It has been implicated in the control of development, growth, immune system function, and carcinogenesis. Although TGF-β1 stimulates wound healing in vivo, the growth of many cell types in vitro is inhibited by this growth factor. In addition, the cellular growth response to TGF-β1 in vitro has been found to be dependent both on cell type and culture conditions. The ability of TGF-β1 to inhibit the growth of carcinoma and melanoma cells is of particular interest because it suggests the possible use of this factor as a chemotherapeutic agent. One recent study has demonstrated a 60% inhibition of A549 lung carcinoma tumor growth in athymic mice by TGF-β1, Twardzik et al, J. Natl. Cancer Inst. 81, 1182-1185 (1989). However, the precise mechanisms of cell growth inhibition by TGF-β1 are not known.

Because cellular response to TGF-β1 is often altered by the presence of other factors, including growth factors and retinoids, which are present in serum, it is advantageous to carry out studies of TGF-β1 action under serum-free conditions. Improved serum-free media were used for the anchorage-dependent growth of A549 human lung carcinoma, MCF-7 human breast carcinoma and B16 mouse melanoma cells. These studies have led to the observation that carcinoma and melanoma cell growth inhibition by TGF-β1 is dependent on the presence of polyunsaturated fatty acids (PUFAs).

It has now been found that the controlled presence of certain specified PUFAs produces a synergistic enhancement of the tumor growth inhibition properties of TGF-β1, resulting in irreversible growth inhibition and cell death. This enhancement can be further potentiated in the case of certain tumors by the addition of a retinoid such as retinoic acid or the retinoid set forth in U.S. Pat. No. 4,326,055. Inhibition of the growth of nontransformed cells by TGF-β1 was not potentiated by PUFAs and was generally found to be reversible.

DESCRIPTION OF THE PREFERRED EMBODIMENT

The TGF-β1 used in the practice of the present invention can be derived from platelets or any other mammalian tissue employing methods known in the art. Additionally, it is known in the art to produce purified TGF-β1 from recombinant cell culture which material is also suitable for purposes of the instant invention. Since TGF-β1 is not species specific it is within the scope of the present invention to employ TGF-β1 from animal sources other than human, for example porcine or bovine sources.

The TGF-β1 compositions to be used in the treatment of neoplastic diseases can be formulated and dosed in a fashion consistent with good medical practice taking into consideration the disorder to be treated, the condition of the individual patient, the site of delivery of the TGF-β1, the method of administration and other factors known to practitioners.

TGF-β1 is prepared for administration by mixing TGF-β1 at the desired degree of purity with physiologically acceptable carriers, i.e. carriers which are non-toxic to recipients at the dosages and concentrations employed. Ordinarily, this will entail combining TGF-β1 with buffers, low molecular weight (less than about 10 residues) polypeptides, proteins, amino acids, carbohydrates including glucose or dextrans, chelating agents such as EDTA and other excipients. TGF-β1 for use in therapeutic administration must be sterile. This is readily accomplished by sterile filtration through membranes known in the art for this purpose. TGF-β1 ordinarily will be stored as an aqueous solution since it is highly stable to thermal and oxidative denaturation, although lyophilized formulations for reconstitution are acceptable.

The dosage of TGF-β1 to be employed is dependent upon the factors described above. As a general proposition, the TGF-β1 should be formulated and delivered to the target neoplastic site at a dosage capable of establishing in the neoplastic tissue a TGF-β1 level greater than about 0.25 ng/gram tissue. Typically, the TGF-β1 concentrations at or near the target neoplastic site should range about from 0.25 to 5.0 ng/gram tissue. These intra-tissue concentrations should be maintained if possible over the treatment period by continuous infusions, sustained release formulations or pegylation or by injection at empirically determined frequencies.

It is, of course, the purpose of the present invention to provide a synergistically effective amount of a desired PUFA to the patient concurrently with the treatment with TGF-β1. This can be readily accomplished by any one of several alternate methods. In one embodiment, the PUFA is admixed with the TGF-β1 in a single dosage form in sufficient amount to provide upon administration a concentration in the range of from about 10 to 1000 μg PUFA per gram tissue at the neoplastic site. The concentration of the TGF-β1 will be in the effective range provided above. Obviously, the ability to employ the fixed combination embodiment will depend on the characteristics of the compounds selected, their solubility and/or their mutual compatibility for the solvents, buffers and carriers employed in the formulation. It is also within the scope of the present invention to employ the active agents in independent dosage forms to be administered either concurrently or in separately scheduled doses. Moreover, it is possible to utilize independent routes of administration for the two agents. Thus, for example, it would be within the scope of the invention to administer the TGF-β1 in the form of a parenteral solution while administering the selected PUFA as an oral dosage form such as a tablet or soft gelatin capsule containing purified PUFAs or a PUFA-containing tissue extract such as fish oil.

The desired PUFA may be provided in the form of a free acid or if desired, as a derivative such as for example as a lower alkyl ester, e.g., the methyl or ethyl esters, which are known materials. The derivatization of the selected PUFA can be employed to influence its solubility or stability, particularly when formulating with the TGF-β1 in a single dosage form or when seeking to use the PUFA in a separate dosage form suitable for sustained release or extended half-life.

The specific PUFAs which can be employed in the present invention include those having from 2 to 6 double bonds, most preferably an n=3 or Ω-3 PUFA. Suitable PUFAs include linoleic, alpha-linolenic, gamma-linolenic, arachidonic, dihomogammalinolenic, eicosapentaenoic, docosahexaenoic acids and derivatives thereof.

As a further aspect of the present invention it is preferred to add a retinoid to the treatment regimen. Suitable retinoids include all trans-retinoic acid, all cis-retinoic acid and the retinoids set forth in U.S. Pat. Nos. 4,105,681; 4,193,931; 4,326,055; 4,396,553 and 4,689,350. The retinoids may be added to the previously described single agent and multiple agent compositions of the instant invention in therapeutically effective amounts known in the art, e.g. 0.1 to 10 mg per kg body weight per day.

The present invention in a preferred embodiment is illustrated by reference to the following example.

EXAMPLE

Materials and Methods

Materials and Cells

Serum-free medium components were obtained and stock solutions were prepared as follows: Crystallized, fatty acid-free bovine serum albumin (BSA) #A 0281 (50 mg/ml in calcium and magnesium-free phosphate buffered saline PBS); soy bean trypsin inhibitor; insulin (20 $\mu$g/ml in 6 mM HCl); transferrin #T 5391 (5 $\mu$g/ml in PBS); hydrocortisone (500 $\mu$g/ml in ethanol, stored in dark under argon at $-20°$ C.); and triiodothyronine (20 nM in 10 nM NaOH) were from Sigma. Porcine TGF-$\beta$1 (in 4 mM HCl, 1 mg/ml BSA) and basic fibroblast growth factor (bFGF)(in 1 mg/ml BSA) were from R & D (Minneapolis, Minn.). Receptor grade epidermal growth factor (EGF)(in 1 mg/ml BSA), vitamin E and liquid RPMI1640 medium were from Gibco. Bovine plasma fibronectin was from Gibco or Sigma. Bovine skin type I collagen was from Collagen Corp. (Palo Alto, Calif.). Fatty acids were from either Sigma or Nu Check Prep (Elysian, Minn.) and were stored in ethanol, under argon, at either $-20°$ C. or $-80°$ C. Similar results were obtained regardless of source or storage temperature. Custom fatty acid-free Dulbecco's modified Eagle's medium/Ham's F12 (DME/F12) was from Specialty Media, Inc., Lavallette, N.J. Milli-Q (Millipore) water was used in all experiments. All other materials were tissue culture grade from Sigma or Gibco. All stocks were made fresh every 2-3 months.

A549 human lung carcinoma cells were from Dr. Lawrence Levine (Brandeis University), and B16-F1 mouse melanoma cells were from The American Type Culture Collection. Cells were maintained at 37° C. (5% $CO_2$) in RPMI1640 medium with 10% fetal calf serum (Hyclone, Logan, Utah) and 15 mM Hepes. B16 melanoma cells were additionally maintained in the presence of 100 units/ml penicillin and streptomycin. Fresh cultures were initiated from frozen stocks every 2-3 months.

Serum-Free Growth of A549 Lung Carcinoma Cells

Growth of A549 cells was carried out by a modification of the method of Brower et al, Cancer Res. 46 798-806 (1986). Tissue culture wells (2 cm$^2$) were treated with 0.3 ml 10 $\mu$g/ml fibronectin in RPMI1640 medium overnight at 37° C., followed by aspiration and similar treatment with type I collagen. Wells were rinsed once with PBS before cell plating. A549 cells (100 mm dish) were washed once and then dissociated with 3 ml 0.05% trypsin/0.53 mM EDTA in PBS, which was removed while the cells were still attached. Trypsin inhibitor (5 ml of 1 mg/ml in RPMI1640) was added and the cells were dispersed and washed 2-times with RPMI1640. Cells (5×10$^3$/well) were plated in 0.5 ml RPMI1640 containing 1 mg/m BSA, 20 $\mu$g/ml insulin, 10 $\mu$g/ml transferrin, 0.5 mM sodium pyruvate, 5 ng/ml bFGF, 5 ng/ml EGF, 2 mM glutamine, 100 nM hydrocortisone, 50 nM sodium selenite, and 3 ng/ml retinoic acid. TGF-$\beta$1, fatty acid, prostaglandins and vitamin E were added 18 to 24 hours after plating, and then cell numbers were determined after an additional 3, 4 or 5-day incubation. Fatty acids and protaglandins were added in 2 ml ethanol or, more recently, after dilution of concentrated stocks (20 mg/ml) into tissue culture medium containing 1 mg/ml BSA (made fresh for each experiment). Treated cells were compared to cells which received vehicle controls in all experiments. All experiments were carried out in triplicate and results are expressed as mean cell number $\pm$SD.

Serum-Free Growth of B16 Melanoma Cells

Tissue culture wells were coated with 3 $\mu$g fibronectin in fatty acid-free DME/F12/RPMI1640 medium (1/1/2) as described above for A549 cells. Cells were incubated with non-enzymatic PBS-based cell dissociation solution (Sigma), then dispersed in DME/F12/RPMI1640 medium followed by 1 wash with the same medium. The growth medium was a modification of that described by Fernandez-Pol et al, Cancer res. 46, 5153-516 (1986). Cells were plated in 0.5 ml fatty acid-free DME/F12/RPMI1640 medium containing 1 mg/ml BSA, 5 $\mu$g/ml insulin, 5 $\mu$g/ml transferrin, 2 mM glutamine, 5 pM triiodothyronine, 10 nM sodium selenite, and 50 nM hydrocortisone. All other additions and determinations were carried out as described above for A549 cells.

RESULTS

Figure 1:
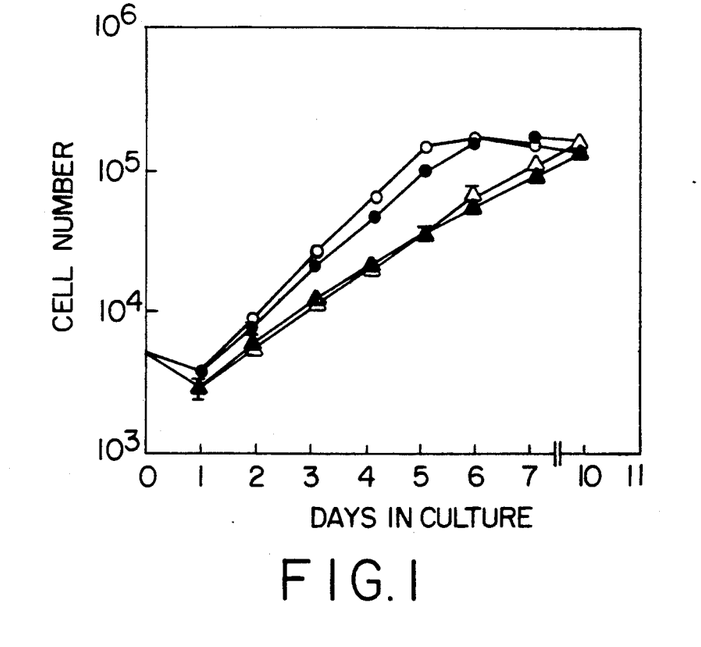
FIG. 1. Anchorage-dependent growth of A549 cells in 10% calf serum and serum-free medium in the presence and absence of TGF-β1. Cells were grown in serum-free medium without (△) or with (▲) 200 pM TGF-β1, or in RPMI1640 medium containing 10% fetal calf serum without (○) or with (●) 200 pM TGF-β1.
Figure 2A:
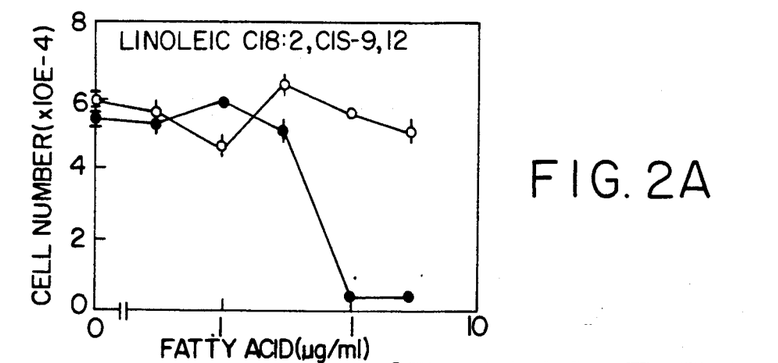
FIG. 2A, 2B, 2C, 2D Effects of fatty acids on A549 cell growth inhibition by TGF-β1. Cells were grown under serum-free conditions with the indicated fatty acids, in the absence (○) or presence (●) of 100 pM TGF-β1. Cell numbers were determined 5 days after TGF-β1 addition. PUFA-dependent inhibition of A549 cell growth by TGF-β1 was observed in 12 independent experiments.
Figure 2B:
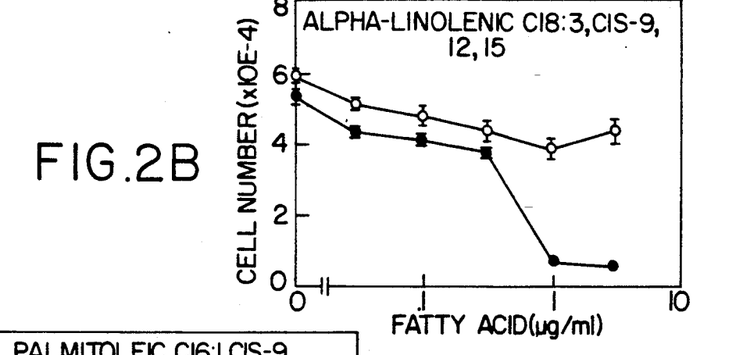
Figure 2C:
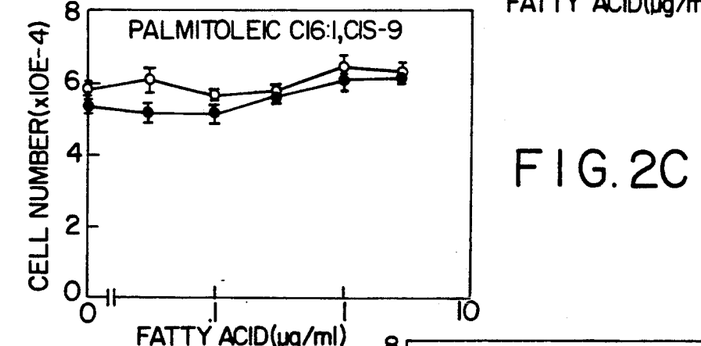
Figure 2D:
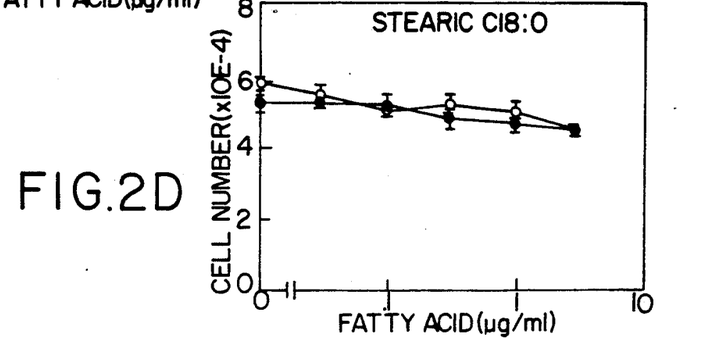

Effects of TGF-$\beta$1 on Growth of A549 Cells in Serum-Containing and Serum-Free Media An improved serum-free medium was developed for the growth of A549 lung carcinoma cells (FIG. 1). The medium is based on the ACL-3 medium developed by Brower et al. Alterations include changes in the concentrations of several factors, elimination of triiodothyronine, and addition of basic FGF and retinoic acid. No lag period was observed when A549 cells were grown in modified ACL-3 medium, and the doubling time was 27.1 h, compared to 36 h reported for growth of these cells in ACL-3 medium. The doubling time in serum-containing medium (18.7 h) was comparable to that reported by Brower et al.

TGF-$\beta$1 (60 pM) has been found to reversibly inhibit the anchorage-dependent growth of A549 cells in medium containing 2% fetal calf serum by 70%, Roberts et al, Proc. Natl., Acad. Sci. USA, 82, 119-123 (1985). In the present study, addition of 200 pM TGF-$\beta$1 inhibited subconfluent A549 cell growth in the presence of 10% fetal calf serum by 33%. Whereas, TGF-$\beta$1 was only able to inhibit the serum-free growth of these cells by 18-20% (FIG. 1).

Inhibition of A549 Cell Growth by TGF-$\beta$1 in the Presence of Exogenous PUFAs Addition of PUFAs at concentrations below 5 $\mu$g/ml had little effect on the serum-free growth of A549 cells. However, the presence of linoleic or alpha-linolenic acid significantly increased the cellular sensitivity to growth inhibition by TGF-$\beta$1. TGF-$\beta$1 inhibited the growth of A549 cells by almost 100%, relative to the cell density at the time of TGF-$\beta$1 addition, when the assay was carried out in the presence of 1-3 $\mu$g/ml linoleic or alpha-linoleic acid (FIG. 2). Similar results were obtained with arachidonic, eicosapentaenoic, and docosahexaenoic acids. The presence of retinoic acid in the growth medium was required for significant PUFA-dependent growth inhibition by TGF-$\beta$1 (data not shown). Unsaturated and monounsaturated fatty acids were unable to increase A549 cellular sensitivity to growth inhibition by TGF-$\beta$1 (FIGS. 2A, 2B, 2C, 2D).

Similar results were obtained with caprylic, lauric, palmitic, and elaidic acids.

Figure 3:
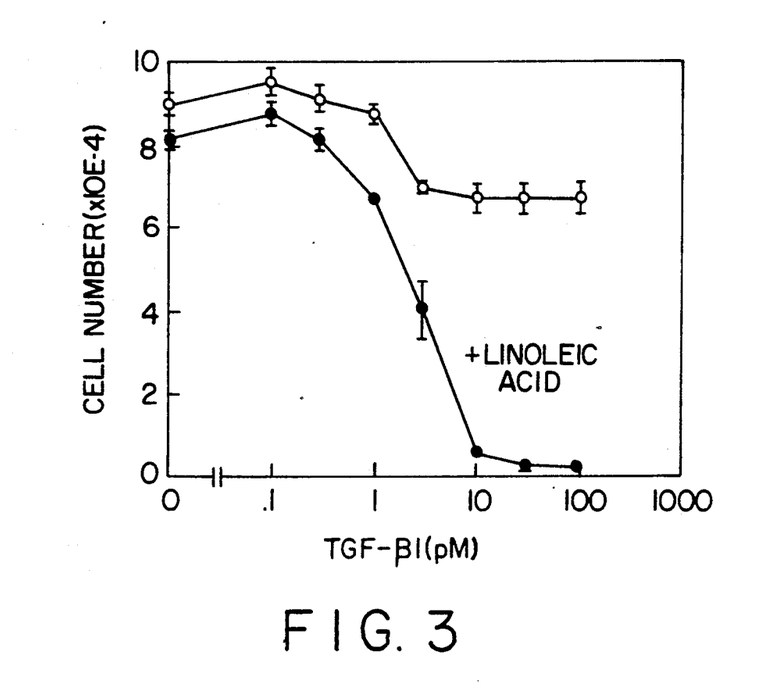
FIG. 3 Dose-response curve for inhibition of A549 cell growth by TGF-β1 in the presence and absence of linoleic acid. Cells were grown under serum-free conditions with the indicated concentrations of TGF-β1 in the absence (○) or presence (●) of 2 μg/ml linoleic acid. Cell numbers were determined 5 days after TFG-β1 addition.
Figure 4A:
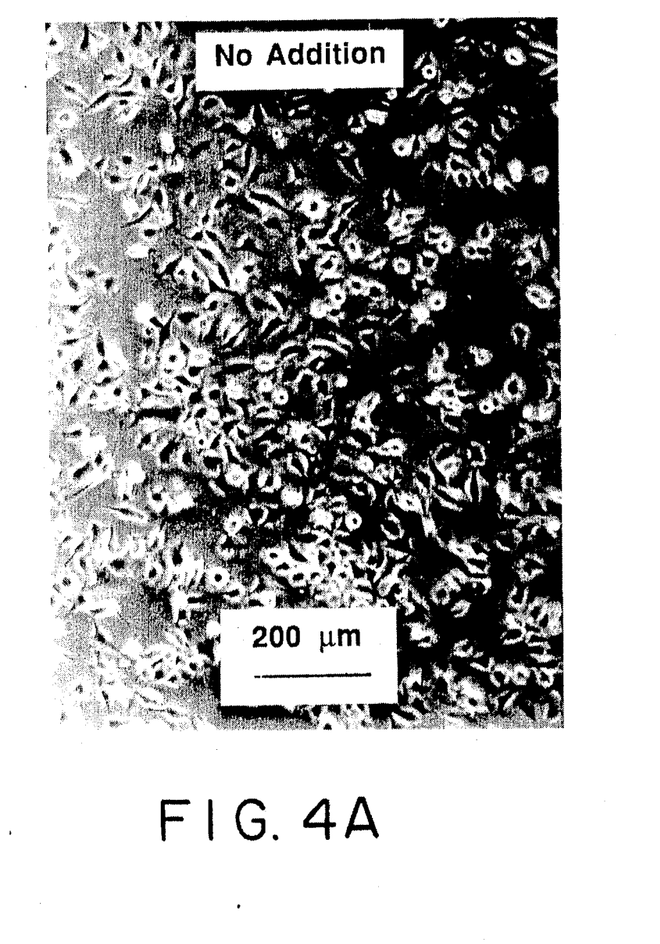
FIGS. 4A, 4B, 4C, 4D Photographs of A549 cells grown in the absence and presence of 1 μg/ml linoleic acid and 25 pM TGF-β1. Cells were grown under serum-free conditions with the indicated additions. Photographs were taken with a Nikon N2000 camera 4 days after fatty acid and TGF-β1 addition.
Figure 4B:
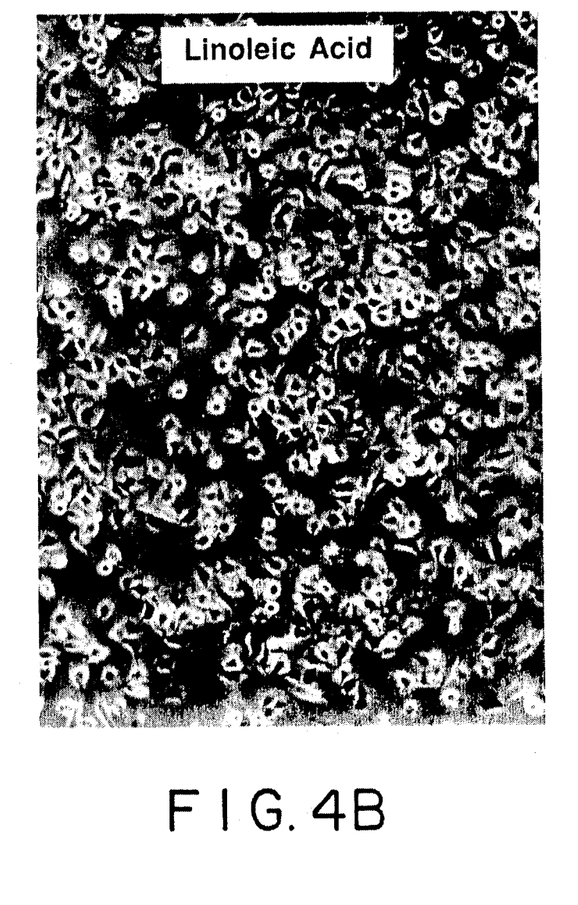
Figure 4C:
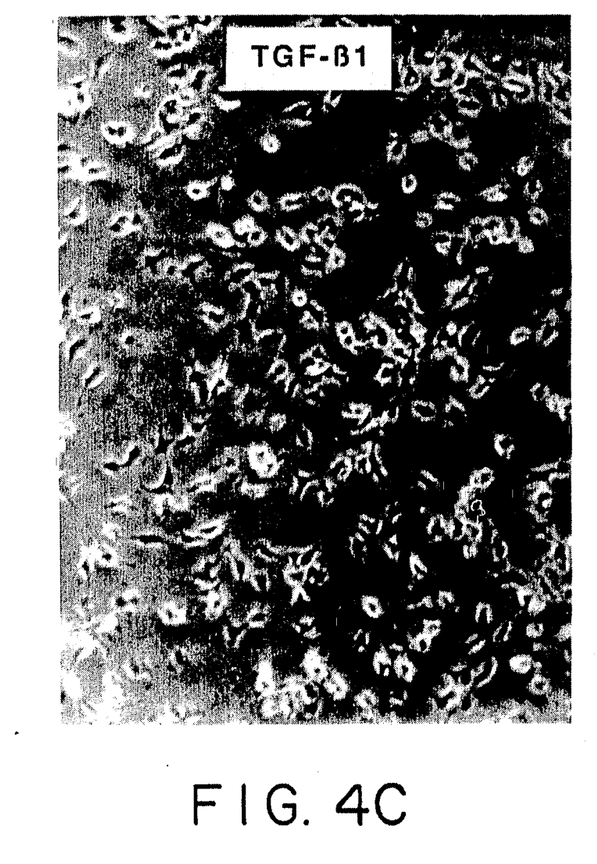
Figure 4D:
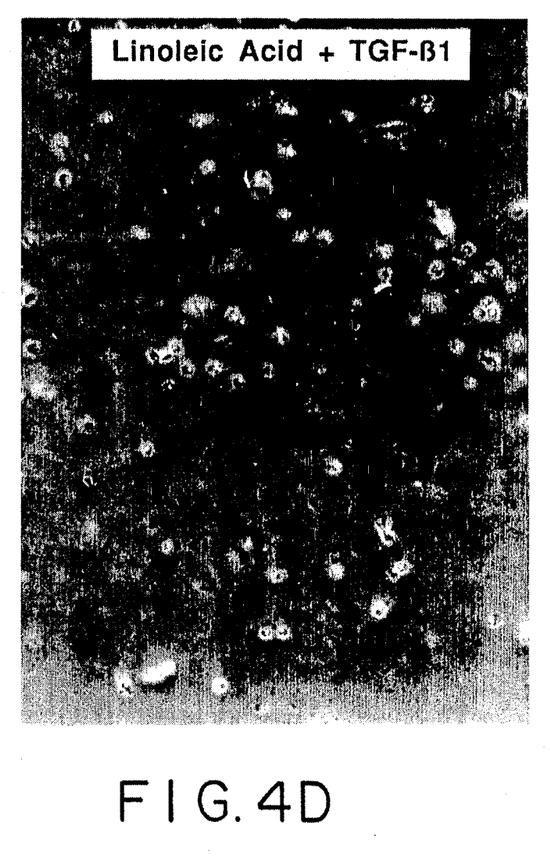

Titrations of TGF-$\beta1$ Revealed a Biphasic Response to this Factor by A549 Cells Sub-picomolar concentrations of TGF-$\beta1$ reproducibly produced a small stimulation of cell growth in the absence or presence of linoleic acid. A similar stimulation of normal rat kidney cell growth by sub-picomolar concentrations of TGF-$\beta1$ under serum-free conditions was observed previously; see Nugent and Newman, J. Biol. Chem. 264 18060–18067 (1989) Picomolar concentrations of TGF-$\beta1$ inhibited A549 cell growth by a maximum of 20% in the absence of linoleic acid, as described above. Titration of TGF-$\beta1$ between 0.5 and 10 pM (0.0125 to 0.25 ng/ml) resulted in a dose-dependent 95–100% inhibition of cell growth in the presence of 2 $\mu$g/ml linoleic acid (FIG. 3). Final cell numbers in the presence of TGF-$\beta1$ were lower than the initial plating density or the cell density at the time of TGF-$\beta1$ addition.

Irreversible Inhibition of A549 Cell Growth by TGF-$\beta1$ in the Presence of PUFAs A549 growth curves carried out in the presence of PUFAs and TGF-$\beta1$ demonstrated that little TGF-$\beta1$-mediated growth inhibition occurred during the first 1–2 days. However, PUFA and TGF-$\beta1$ treatment caused a complete cessation of growth by day 3 and resulted in destruction and loss of attached cells during subsequent incubation. FIGS. 4A, 4B, 4C, 4D, demonstrates that treatment of cells with linoleic acid and TGF-$\beta1$ resulted in both cell growth inhibition and subsequent cell destruction. This observation was confirmed by analysis of trypan blue exclusion by untreated and TGF-$\beta1$-treated cells. After growth in the presence of linoleic acid and TGF-$\beta1$, approximately 80% of the remaining cells were non-viable on the basis of trypan blue uptake. These results were also confirmed by direct re-plating of cells. Cells were grown in the presence of 1 $\mu$g/ml linoleic acid with or without TGF-$\beta1$ for 4 days. Untreated wells contained an average of $10.24 \times 10^4$ cells and TGF-$\beta1$-treated wells contained $0.27 \times 10^4$ cells. Trypsinization and re-plating of the TGF-$\beta1$-treated cells in medium containing 10% fetal calf serum resulted in the isolation of only a few colonies. Untreated cells were easily re-plated at high efficiency.

Growth of nontransformed fibroblasts and epithelial cells under serum-free conditions in the presence of PUFAs was found to be less sensitive to inhibition by TGF-$\beta1$ than the growth of tumor cells. In addition, inhibition of the growth of nontransformed cells by TGF-$\beta1$ was not potentiated by PUFAs, and has generally been found to be reversible (data not shown).

Role of PUFAs in A549 Cell Growth Inhibition by TGF-$\beta1$

Figure 5:
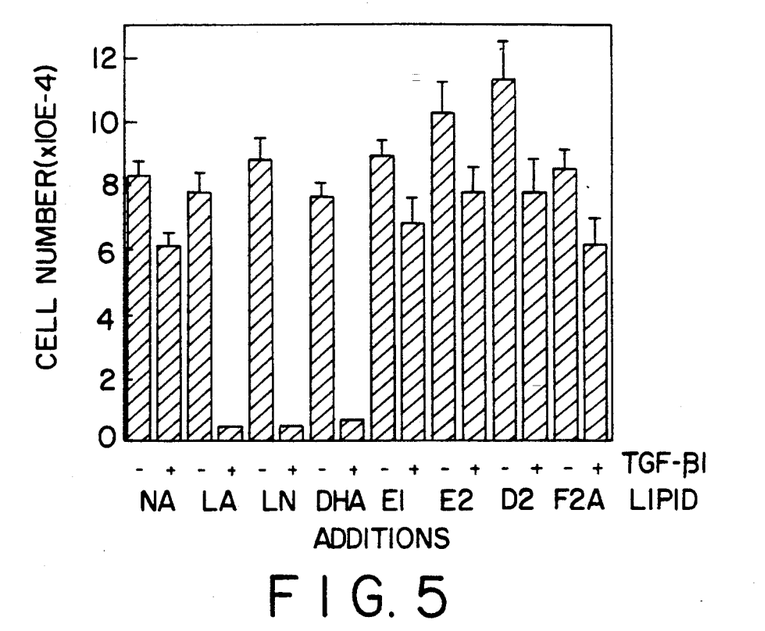
FIG. 5 Effects of fatty acids and prostaglandins on A549 cell growth inhibition by TGF-β1. Cells were grown under serum-free conditions with 1 μg/ml of the indicated lipid, in the absence (−) or presence (+) of 40 pM TGF-β1. Cell numbers were determined 4 days after TGF-β1 addition. NA, no additions; LA, linoleic acid; LN, alpha-linolenic acid; DHA, docosahexaenoic acid; E1, E2, D2, F2A, prostaglandins $E_1$, $E_2$, $D_2$, and $F_2$ alpha respectively.

The possibility that a PUFA metabolite may be the mediator of A549 cell growth inhibition by TGF-$\beta1$ was tested. FIG. 5 demonstrates that, although 1 $\mu$g/ml linoleic, alpha-linolenic or docosahexaenoic acid were able to mediate growth inhibition by TGF-$\beta1$, prostaglandins $E_1$, $E_2$, $D_2$, and $F_2$alpha at similar concentration were unable to act synergistically with TGF-$\beta1$ to inhibit the growth of A549 cells.

Figure 6:
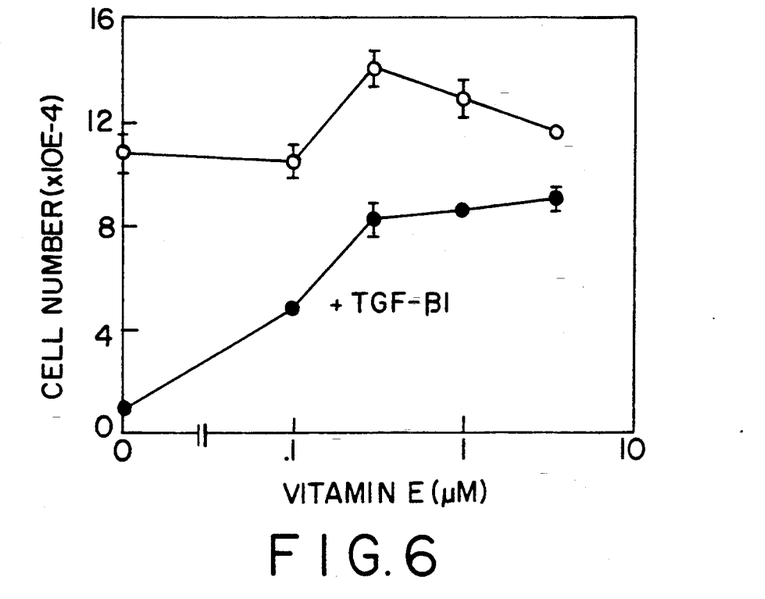
FIG. 6 Reversal of linoleic acid and TGF-β1-mediated A549 cell growth inhibition by Vitamin E. Cells were grown under serum-free conditions with 2 μg/ml linoleic acid and the indicated concentrations of vitamin E, in the absence (○) or presence of (●) of 25 pM TGF-β1. Cell numbers were determined 5 days after TGF-β1 and vitamin E addition. Similar results were obtained in 3 independent experiments.

Linoleic acid (an n-6 fatty acid), alpha-linolenic acid and docosahexaenoic acid (n-3 fatty acids) serve as precursors for the biosynthesis of different cyclooxygenase or lipoxygenase products. Thus, the results described above suggest that PUFAs themselves, or some product common to all PUFAs, must be responsible for mediating growth inhibition by TGF-$\beta1$. PUFAs are susceptible to peroxidation, resulting in the generation of toxic degradation products. Thus, cell growth inhibition by 1 $\mu$g/ml linoleic acid and 25 pM TGF-$\beta1$ was examined in the presence and absence of the antioxidant vitamin E. FIG. 6 demonstrates that vitamin E was able to prevent A549 cell growth inhibition by TGF-$\beta1$ in the presence of linoleic acid. Vitamin E did not reverse TGF-$\beta1$-mediated growth inhibition completely.

Polyunsaturated Fatty Acid-Dependent Inhibition of B16 Melanoma Cell Growth by TGF-$\beta1$ In order to determine if PUFAs play a general role in tumor cell growth inhibition by TGF-$\beta1$, a second cell type was examined. The B16 mouse melanoma cell line was chosen because anchorage-independent growth of this cell type in the presence of serum is inhibited by TGF-$\beta1$, while anchorage-independent growth of B16 cells in serum-free medium is stimulated by TGF-$\beta1$. These results suggest that B16 cell growth inhibition by TGF-$\beta1$ may be dependent on unidentified factors, such as PUFAs, contained in serum.

Figure 7A:
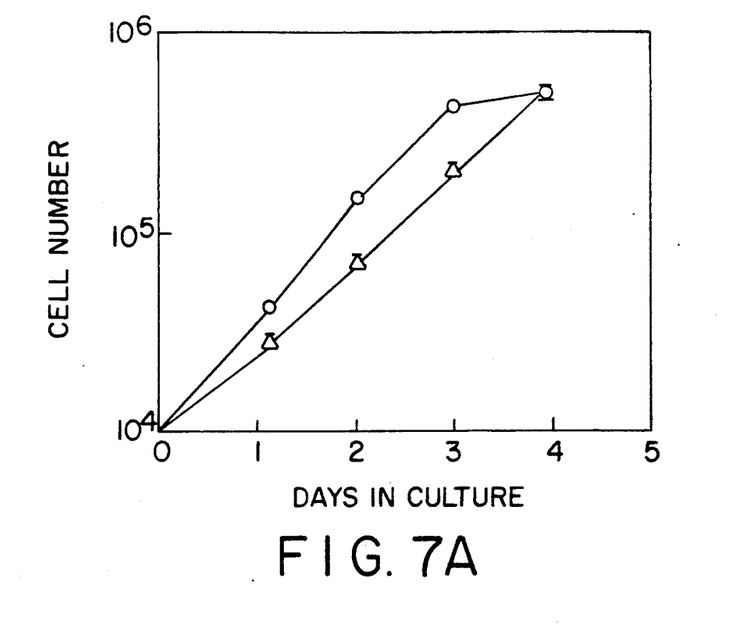
FIG. 7A Anchorage-dependent growth of B16 melanoma cells in 10% fetal calf serum and serum-free medium. Cells ($1 \times 10^4$/well) were grown in serum-free medium (△) or RPMI1640 medium containing 10% fetal calf serum (○).

As described above for A549 cells, the present studies were dependent on the development of an improved serum-free medium for the anchorage-dependent growth of B16 melanoma cells. The medium is based on DME/F12+H+F developed by Fernandez-Pol et al. The modifications include the use of fibronectin, rather than serum, for promotion of cell attachment, the elimination of prostaglandin $E_1$, and the addition of crystalized fatty acid-free BSA. The basal medium was also changed, and is composed of a mixture of DME, Ham's F12 and RPMI1640. B16 cell doubling times in the presence of serum and serum-free medium were 13.4 h and 15.8 h respectively (FIG. 7A).

Figure 7B:
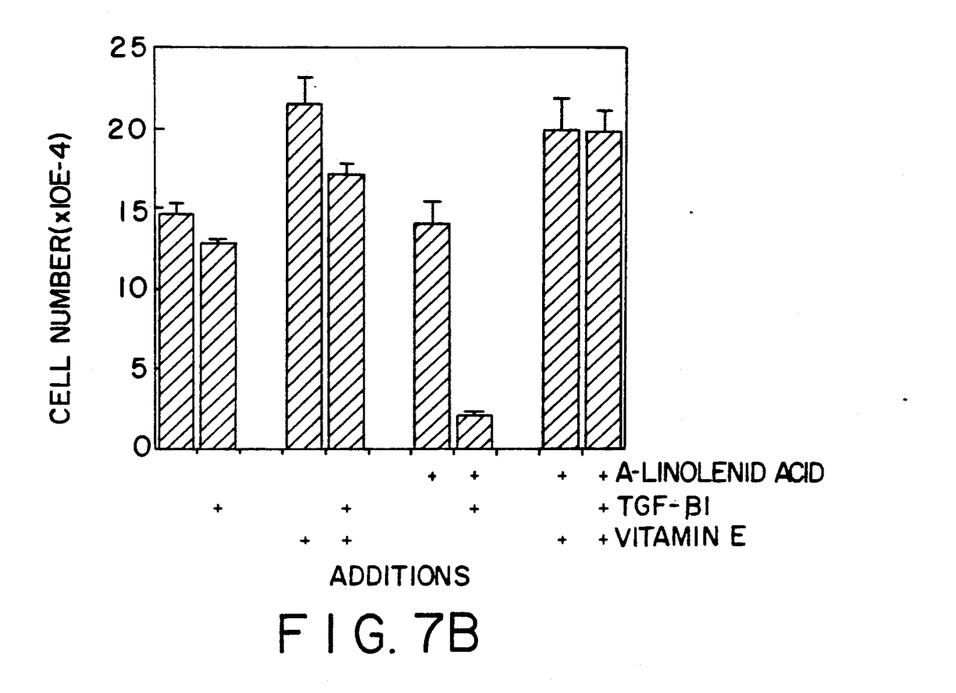
FIG. 7B Effects of alpha-linolenic acid and vitamin E on B16 cell growth inhibition by TGF-β1. Cells ($5 \times 10^3$/well) were grown under serum-free conditions in the absence or presence of 10 μg/ml alpha-linolenic acid, 100 pM TGF-β1 and (or) 1 μM vitamin E. Cell numbers were determined 3 days after fatty acid, TGF-β1 and vitamin E addition. Similar results were obtained in 3 independent experiments.

Treatment of B16 cells with 100 pM TGF-$\beta1$ under serum-free anchorage-dependent conditions resulted in a 10–15% inhibition of growth, as described above for A549 cells (FIG. 7B). Addition of 10 $\mu$g/ml alpha-linolenic acid alone had little effect on the growth of the cells, but the presence of alpha-linolenic acid allowed TGF-$\beta1$ to inhibit cell growth by 85%. Similar results were obtained with linoleic, gamma-linolenic, arachidonic and docosahexaenoic acids. As described for A549 cells, long-term treatment with TGF-$\beta1$ and PUFAs caused an irreversible inhibition of B16 cell growth. Inhibition of the growth of B16 cells by TGF-$\beta1$ in the presence, but not in the absence, of alpha-linolenic acid was reversed by vitamin E (FIG. 7B). Alpha-linolenic acid also increased B16 sensitivity to growth inhibition by TGF-$\beta1$ in the presence of serum. The synergistic inhibitory effect of TGF-$\beta1$ and PUFAs in the presence of serum was dependent on the addition of retinoic acid, and was largely reversed by addition of both vitamin E and sodium selenite.

What is claimed is:

1. A method for treating neoplastic diseases in a host which method comprises treating such host with synergistically effective doses of transforming growth factor beta 1 (TGF-$\beta1$) and a polyunsaturated fatty acid (PUFA) or derivative.

2. The method of claim 1 wherein said TGF-$\beta1$ and said PUFA are provided combined in a single dosage form.

3. The method of claim 1 wherein said TGF-β1 and said PUFA are provided concomitantly in separate dosage forms.

4. The method of claim 3 wherein said TGF-β1 is provided in a parenteral dosage form and said PUFA is provided in an oral dosage form.

5. The method of claim 1 wherein said PUFA has 2 or more double bonds.

6. The method of claim 5 wherein said PUFA is an acid selected from linoleic, alpha-linolenic, gamma-linolenic, arachidonic, dihomogammalinolenic, eicosapentaenoic and docosahexaenoic acids, or an animal tissue extract containing polyunsaturated fatty acids.

7. The method of claim 1 wherein said treatment also involves administration of an effective amount of a retinoid.

8. The method of claim 1 wherein said TGF-β1 is recombinant human TGF-β1.

9. The method of claim 1 wherein said neoplastic disease in said host is a carcinoma.

10. The method of claim 1 wherein said neoplastic disease in said host is a melonoma.

11. A pharmaceutical composition for treatment of a neoplastic disease in a host comprising minor, synergistically effective amounts of TGF-β1 and a PUFA or derivative, and a major amount of a pharmaceutical adjuvant.

12. The composition of claim 11 wherein TGF-β1 is present in an amount sufficient to provide a concentration of from 0.25 to 5 nanograms/gram tissue at the neoplastic target site in said host and said PUFA is present in an amount sufficient to provide a concentration of from 10 to 1000 micrograms/gram tissue at the neoplastic target site in said host.

13. The composition of claim 12 wherein said TGF-β1 is recombinant human TGF-β1.

14. The composition of claim 13 wherein said PUFA has 2 or more double bonds.

15. The composition of claim 14 wherein said PUFA is selected from linoleic, alpha-linolenic, gamma-linolenic, arachidonic, dihomogammalinolenic, eicosapentaenoic or docosahexaenoic acids.

16. The composition of claim 12 wherein a minor effective amount of a retinoid is also present.

* * * * *

UNITED STATES PATENT AND TRADEMARK OFFICE
CERTIFICATE OF CORRECTION

PATENT NO. : 5,147,854
DATED : September 15, 1992
INVENTOR(S) : MICHAEL J. NEWMAN It is certified that error appears in the above-identified patent and that said Letters Patent is hereby corrected as shown below:

On the title page: Item [54] and Column 1, line 1

"TGF-B COMPOSITIONS AND METHOD"

Should be "TGF-ß COMPOSITIONS AND METHOD"

Signed and Sealed this

Fourteenth Day of September, 1993

Attest:

BRUCE LEHMAN

*Attesting Officer*  *Commissioner of Patents and Trademarks*